United States Patent [19]

Kunicki et al.

[11] Patent Number: 4,710,381

[45] Date of Patent: Dec. 1, 1987

[54] METHOD FOR MAINTAINING INTACT, NON-DEGRADED FACTOR VIII/VON-WILLEBRAND FACTOR DURING BLOOD PROCESSING

[75] Inventors: Thomas J. Kunicki, Brookfield; Robert R. Montgomery, Mequon, both of Wis.

[73] Assignee: The Blood Center of Southeastern Wisconsin, Milwaukee, Wis.

[21] Appl. No.: 612,873

[22] Filed: May 22, 1984

[51] Int. Cl.$^4$ .................... A61K 35/16; C07K 15/00
[52] U.S. Cl. .................................. 424/101; 530/381; 530/830; 530/831; 530/383
[58] Field of Search ................ 424/101; 530/381, 830, 530/831, 383

[56] References Cited

U.S. PATENT DOCUMENTS

| | | |
|---|---|---|
| Re. 29,698 | 7/1978 | Fekete et al. . |
| 4,022,758 | 5/1977 | Andersson et al. . |
| 4,203,891 | 5/1980 | Rock . |
| 4,221,780 | 9/1980 | Cort . |
| 4,235,881 | 11/1980 | Cort . |
| 4,278,594 | 7/1981 | Amrani . |
| 4,302,445 | 11/1981 | Pla et al. . |
| 4,305,871 | 12/1981 | Shanbrom . |
| 4,348,384 | 9/1982 | Horikoshi et al. . |
| 4,359,463 | 11/1982 | Rock . |
| 4,361,509 | 11/1982 | Zimmerman et al. . |
| 4,364,861 | 12/1982 | Mitra et al. . |
| 4,383,989 | 5/1983 | Rock . |
| 4,386,068 | 5/1983 | Mitra et al. . |
| 4,391,746 | 7/1983 | Mitra et al. . |
| 4,395,396 | 7/1983 | Eibl et al. . |
| 4,404,131 | 9/1983 | Schwarz et al. . |
| 4,404,132 | 9/1983 | Mitra . |
| 4,406,886 | 9/1983 | Bier et al. . |

OTHER PUBLICATIONS

Kinlough et al—Chem. Abst. vol. 65 (1966), p. 5984g.
Switzer et al—Chem. Abst. vol. 98 (1983), p. 105045v.
Deykin et al—Chem. Abst. vol. 93 (1980), p. 199,511r.
Switzer et al—Chem. Abst. vol. 93 (1980), p. 236,051p.
"Specific Factor VIII-Related Antigen Fragmentation: An In Vivo and In Vitro Phenomenon", *Blood,* vol. 60, p. 930, et seq., Oct. 1982.
Human Platelet Calcium-Activated Protease (CAP): Degradation of Fibrogen and Modification of von Willebrand Factor, *Blood,* vol. 62, (Supp. 1), p. 260a, Nov. 1983.
"Purification of Human Platelet Calcium-activated Protease", the *Journal of Biological Chemistry,* vol. 258, No. 11, pp. 7168-7174, Jun. 1983, article identifies the calcium-activated protease responsible for the degradation of von Willebrand factor.
"Cleavage of Human Platelet Fibrogen and Factor VIII/von Willebrand Factor (FVIII/vWf) by Endogenous Calcium-Activated Protease", received for publication by The Journal of Clinical Investigation, May 24, 1983, not published, describes cleavage of FVII/vWf by calcium-activated protease based on preliminary evidence.
"Factors Influencing the Multimeric Structure of Human Platelet von Willebrand Factor", received for publication by *Blood,* Oct. 7, 1983, revised and published Aug. 1, 1984 under the title Cleavage of Human von Willebrand Factor by Platelet Calcium-Activated Protease.
"Presence of a von Willebrand Factor (vWf) Fragment in Type IIa von Willebrand's Disease (vWd)", *Clinical Research,* vol. 32, p. 316A, 1984.
"Inhibition of von Willebrand Factor Fragmentation in Stored Plasma Containing Platelets by Inhibitors of the Calcium-Activated Protease", *American Heart Association,* (presented at 57th Meeting of American Heart Association, Nov. 1984).
"Understanding von Willebrand's Disease", *The National Hemophilia Foundation* 1978, background pamphlet describing von Willebrand's disease.

*Primary Examiner*—Sam Rosen
*Attorney, Agent, or Firm*—Andrus, Sceales, Starke & Sawall

[57] ABSTRACT

A method for maintaining intact, non-degraded von Willebrand factor by preventing the action of calcium activated protease(s) responsible for degradation of the factor. The action of the calcium activated protease(s) may be avoided by removing the blood platelet source of the protease(s), by filtering or centrifugal separation, or by inactivating the protease with a chelating agent removing the calcium, by a protease inhibitor, or an alkylating agent.

20 Claims, No Drawings

METHOD FOR MAINTAINING INTACT, NON-DEGRADED FACTOR VIII/VON-WILLEBRAND FACTOR DURING BLOOD PROCESSING

The present invention relates to a method for maintaining intact, non-degraded factor VIII/von Willebrand factor during the processing of blood, plasma, and plasma fractions.

Blood plasma contains a number of protein compounds, often termed factors, that provide certain properties to the blood or carry out physiological functions. One such factor is termed factor VIII (FVIII) or the procoagulant factor (FVIIIC) and assists in the clotting action of the blood. The absence of factor VIII causes the prolonged bleeding of hemophilia. For this reason factor VIII is often termed the anti-hemophilic factor (AHF) or antihemophilic globulin (AHG). Hemophilia occurs in approximately 1 out of 6,000 males.

It is known that factor VIII exists in blood plasma in a molecular complex with another protein factor. This other protein factor is usually termed von Willebrand factor (vWf) after the discoverer of the disease associated with abnormalities in this factor. The von Willebrand factor is also termed factor VIII related antigen (VIIIR:Ag). The molecular complex is termed the factor VIII molecular complex (FVIII/vWf) and is comprised of von Willebrand factor and factor VIII.

The absence of von Willebrand factor in the blood causes an abnormality with the blood platelets, or thrombocytes, that prevents platelet adhesion to the walls of a damaged blood vessel and the maintenance of vascular integrity. The result is the propensity to bruising, nose bleeds, intestinal bleeding, and the like comprising von Willebrand's disease. The deficiency or abnormality in the von Willebrand factor occurs in about 2 to 5 persons out of 1,000 males and females.

Hemophilia and von Willebrand's disease are treated by the venous infusion of concentrated FVIII/vWf obtained from blood plasma. The FVIII/vWf concentrate provides the factors absent in the patient's blood. However, it is now recognized that treatment of von Willebrand's disease with such concentrate is less effective because the von Willebrand factor portion is altered during normal, commercial preparation of the concentrate. See the article entitled "Specific Factor VIII-Related Antigen Fragmentation: An in vivo and in vitro Phenomenon" by Robert R. Montgomery and Janet Johnston in *Blood*, Volume 60, page 930 et seq, October, 1982. Further, when hemophiliacs are treated with the concentrate, the altered von Willebrand factor is infused in the patient and results in abnormality of the von Willebrand factor in the hemophiliac patient's own plasma. This might result in paradoxical bleeding of patients treated for hemophilia with such concentrate.

As noted in the aforesaid article, two alterations of the von Willebrand factor have been observed. One is a loss of the higher molecular weight multimers of the factor VIII/vWf. The second is the production of a relatively low molecular weight fragment, previously known at "VIIIR;Ag fragment" and now known as "vWfrag." At present, both of these phenomena are believed to be proteolytic events.

The present invention is directed to a method for maintaining the von Willebrand factor portion without the alteration or degradation that has heretofore occurred in processing blood or portions thereof. The FVIII/vWf molecular complex with the intact, nondegraded von Willebrand factor portion thus obtained may be used to provide more efficacious treatment of both von Willebrand's disease and hemophilia.

The method of the present invention stems from the inventors' discovery that calcium activated protease(s) present in blood platelets causes the alteration of the von Willebrand factor. See *Blood*, Vol. 62 (Supp 1), page 260a, November 1983 by Kunicki, Montgomery, et al. Under normal conditions the calcium activated protease(s) is contained within whole, integral platelets and cannot react with the von Willebrand factor. However, when platelets are ruptured or fragmented, as during preparation of FVIII/vWf concentrate by common commercial methods, the calcium activated protease(s) is released to degrade the von Willebrand factor. The loss of integrity of the platelets can occur through the centrifugal forces used to separate the plasma from the cells and, more particularly, from the freezing and thawing of the plasma occurring in commercial processing.

By avoiding the action of the protease(s) on the von Willebrand factor portion in the present method, the functional integrity of the FVIII/vWf can be preserved.

The action of the calcium activated protease(s) on the von Willebrand factor may be avoided by removing the platelet source of the protease(s) from the plasma or by inactivating the protease(s). The protease(s) may be inactivated by removing the calcium necessary for activation, as through chelation, or by inhibiting the protease(s).

The process thus permits the recovery of intact, non-degraded von Willebrand factor. The term "non-degraded" as used herein connotes the fact that cleavage of the monomers forming the polymeric structure of the factor by the protease is avoided or diminished. "Intact" as used herein connotes the fact that the alteration of the polymeric structure by the protease is avoided or diminished.

The method of the present invention, may, perhaps best be understood from the following review of current techniques of preparing FVIII/vWf concentrate initially presented below. Whole human blood is drawn from a donor, usually into a plastic bag. An anticoagulant, such as acid-citrate-dextrose is added. The blood is then centrifuged. In a commercial plasmapheresis center, the blood is typically centrifuged at 3,8000 gs for 5 to 10 minutes. This separates the red and white blood cells and the platelets from the plasma. The separated cells and platelets may be returned to the donor, transfused to a patient, or used to manufacture blood products.

Under ideal conditions, the plasma, prepared as described above, is relatively depleted of platelets and is commonly termed "platelet poor plasma". As a practical matter, the level of platelets in this plasma is not carefully controlled. The plasma is frozen and shipped to commercial supply houses that thaw the plasma and separate out various plasma components including FVIII/vWf concentrate.

A blood bank may take the whole blood and subject it to lower speed centrifugal separation, for example, 1000 gs for 10 min. This separates off the red and white blood cells but leaves the majority of the platelets in the plasma. Such plasma is commonly termed "platelet rich plasma". The platelet rich plasma is subjected to an additional centrifugal separation, for example, 3800 gs for 5 to 10 mins. to remove platelets from the plasma to produce platelet poor plasma. The separated platelets may be used for platelet transfusion and the platelet poor plasma frozen and used to prepare a FVIII/vWf concentrate by cryoprecipitation. A concentrate so prepared is termed a "cryoprecipitate".

As noted above, the resulting concentrate has altered von Willebrand factor. This is due to the fragmentation or rupture of the platelets both by the centrifugal action and the freezing and thawing of the plasma. Rupture of the platelets releases the calcium activated protease(s) that alters the von Willebrand factor. Processing times cause the von Willebrand factor to be subjected to the calcium activated protease for periods well in excess of those required to produce undesired degradation.

In accordance with the present invention, alteration of the von Willebrand factor is prevented by avoiding the action of the degrading calcium activated protease(s) on the von Willebrand factor. The specific protease or proteases are calcium activated, sulfhydryl-dependent neutral proteases. Calcium-activated proteases purified from human platelets (See Yoshida N., Weksler B., and Nachman R.,: Journal of Biological Chemistry, Vol. 258, pages 7168–7174, 1983) or other cell sources have common structural features and are composed of two different polypeptide subunits, of molecular weight 80,000 daltons and 27,000 daltons, the larger subunit apparently containing the active site of the enzyme. These proteases will hereinafter, and in the claims, continue to be referred to as calcium activated protease. In medical and scientific literature the protease is also termed calcium dependent protease. As noted supra, this protease is found in the platelets of the blood and is released when the platelets are ruptured when the blood or plasma is processed.

Typically, the method of the present invention will be carried out on platelet poor plasma although, as noted below, it can occur elsewhere in the manufacture of the FVIII/vWf concentrate.

One approach for carrying out the method of the present invention is to remove the platelets from the blood or plasma, thereby to remove the calcium activated protease(s). The term "plasma" as used in this description and in the claims is deemed to include both plasma and fractions thereof. Plasma with no detectible platelets is termed "platelet free plasma".

A preferred technique for obtaining such removal is to pass plasma, such as platelet poor plasma, through a filter sufficiently small to remove the platelets and any platelet fragments. A filter separating at sizes of 0.45 microns would retain whole platelets, while a filter separating at the 0.1 micron size would remove platelet fragments as well as the platelets. A molecular sieve or membrane filter is suitable for use in filtering the plasma. Suitable filters may comprises those sold by Gelman Sciences, Inc. of Ann Arbor, Mich. under the trademark "Acrodisc" or Millipore Corp. of Bedford, MA. After filtering, the plasma filtrate without the platelets, i.e. platelet free plasma, may be used to prepare the FVIII/vWf concentrate in accordance with existing commercial techniques.

The advantage to filtration is that it is a purely mechanical process that does not involve the addition of chemical agents to the plasma. This is of significance since the concentrate obtained from the plasma will ultimately be infused into a human patient. It also results in minimum disruption to the platelets, reducing the possibility that the process of removing the platelets might itself rupture the platelets and release the calcium activated protease.

Centrifuging beyond that necessary to produce platelet poor plasma can be used to remove platelets and platelet fragments from the plasma. For example, centrifuging platelet poor plasma at a force of 20,000 gs for 10 minutes would be adequate to remove virtually all whole platelets and the bulk of the platelet fragments from the plasma. In a preferred embodiment of the invention, directed specifically to maintaining the FVIII/vWf intact and non-degraded, the majority of the platelets, for example 80%, are removed at low speeds to avoid rupture of the platelets and release of the calcium activated protease. The remaining 20% of the platelets are removed at high speed to insure complete removal.

Yet another technique for removing platelets and fragments would be through the use of an antibody specific to the platelets. Such an antibody may be covalently linked to a solid support, such as cyanogen bromide-activated agarose beads, in an immunoaffinity separation column. The plasma is passed through the column. The platelets attach to the antibodies in the column and are removed from the plasma passing through the column. Antibodies suitable for use in carrying out such a separation are described in U.S. patent application Ser. No. 563,102 filed Dec. 9, 1983 by Robert R. Montgomery and Thomas J. Kunick now abandoned, and the hybridomas producing these antibodies bear ATCC Registry Nos. HB8352 and HB8353.

The second major approach to avoiding degradation of the von Willebrand factor portion of the FVIII/vWf molecular complex is to block the action of the calcium activated protease(s) on the von Willebrand factor portion. Since the protease(s) requires calcium to be activated, if the calcium is not available in a reactive form, the protease(s) cannot be activated.

The addition of a chelating agent will remove calcium ions from the plasma, preventing activation of the protease(s). The chelating agent may be preferably be a compound having a high affinity for divalent cations, and particularly calcium ions. The affinity of such a chelating agent for divalent cations is expressed as a binding constant or affinity constant (Ka). For effective chelation of calcium, a Ka of 10 or greater, (expressed as the logarithm to the base 10 of the constant is preferred. A suitable agent may comprise EDTA (ethylenediaminetetraacetic acid) or EGTA (ethyleneglycol-bis-($\beta$-aminoethyl ether)-N,N,N',N'-tetraacetic acid). It will be appreciated that any such agent so used must be safe for use with humans at the concentration to which humans are ultimately subjected.

Tests employing EDTA and EGTA chelating agents indicate that at least 1 micromole of either agent per $10^9$ platelets is normally sufficient. Adding the chelating agent early in the processing of the blood insures application to the platelets before damage. Thus, the chelating agent may be added as soon as possible after drawing whole blood into citrate anticoagulent. This occurs prior to centrifugation of the platelets. Under conditions encountered in a blood bank in which a platelet transfusion is obtained, the chelating agent should be added to the platelet poor plasma after platelet separation.

Another technique for inactivating the calcium activated protease is to add an inhibitor of the calcium activated protease(s) to the plasma. The low molecular weight protease inhibitors leupeptin or antipain are known to inhibit the calcium activated protease. Tests employing leupeptin and antipain inhibitors indicate that at least 80 micromoles of either inhibitor per $10^9$ platelets is normally sufficient to provide inhibition. The inhibiters may be added at the same points in the processing as described in connection with the chelating agents, above.

Another approach would be to modify or remove the sulfhydryl group of the calcium activated protease(s). If the sulfhydryl group is removed or altered, the chemical activity of the protease(s) is altered and the degradation of the von Willebrand factor avoided. For this purpose, alkylating agents may be used. The alkylating agent modifies the sulfhydryl portion of the protease molecule and thus renders it ineffective with respect to the von Willebrand factor. A suitable alkylating agent may comprise NEM (N-ethylmaleimide). Another alkylating agent is IAA (iodoacetimide). Tests employing NEM indicate that at least 1 micromole of this inhibitor per $10^9$ platelets is normally sufficient to provide inhibition of the protease(s).

What is claimed is:

1. A method of preparing blood or plasma for the extraction of intact, non-degraded FVIII/vWf, the blood or plasma containing FVIII/vWf and cellular sources of a calcium activated protease capable of cleaving the FVIII/vWf, said method including the step of removing substantially all cellular sources of the calcium activated protease from the blood or plasma while avoiding release of the protease from the cellular sources prior to or during removal of the cellular sources from the blood or plasma.

2. The method according to claim 1 wherein the blood or plasma includes platelets comprising a source of the calcium activated protease and wherein the method is further defined as removing substantially all platelets and platelet fragments from the blood or plasma.

3. The method according to claim 1 further defined as removing the cellular sources of the calcium activated protease by centrifugation.

4. The method according to claim 2 further defined as obtaining platelet poor plasma and thereafter removing substantially all the platelets and platelet fragments from the platelet poor plasma by a centrifugation comprising up to 20,000 g for up to 10 minutes.

5. The method according to claim 4 further defined as obtaining the platelet poor plasma by subjecting blood or plasma to a separating centrifugation employing forces lower than those used to remove the platelets and platelet fragments from the platelet poor plasma.

6. The method according to claim 1, further defined as removing the cellular sources of the calcium activated protease at least in part by filtration.

7. The method according to claim 6 further defined as passing plasma through a filter capable of retaining particles 0.1 micron in size and larger.

8. The method according to claim 6 further defined as passing plasma through a filter capable of retaining particles in a range of 0.1 to 0.45 microns.

9. The method according to claim 6 further defined as obtaining platelet poor plasma and filtering the platelet poor plasma.

10. The method according to claim 9 further defined as obtaining the platelet poor plasma by subjecting blood or plasma to a separating centrifugation at forces sufficiently low that rupture of the platelets is avoided.

11. The method according to claim 2 further defined as subjecting the blood or plasma to an antibody specific to the platelets and platelet fragments for removing the platelets and platelet fragments.

12. The method according to claim 11 further defined as subjecting the blood or plasma to antibodies, the producing hydridomas of which bear ATCC Registry Nos. HB8352 or HB8353.

13. The method according to claim 1, further defined as including the step of purifying FVIII/vWf from the blood or plasma so treated.

14. A method of preparing blood or plasma for the extraction of intact, non-degraded FVIII/vWf, the blood or plasma containing platelets and FVIII/vWf, said platelets comprising a source of a calcium activated protease capable of cleaving the FVIII/vWf, said method including the steps of obtaining platelet poor plasma while avoiding release of the protease from the platelets and adding a chelating agent to the platelet poor plasma to prevent calcium in the plasma from activating the protease.

15. The method according to claim 14 further defined as adding a chelating agent having binding constant of 10 or greater expressed as the logarithm to the base 10 of the constant.

16. The method according to claim 14 further defined as adding a chelating agent selected from a class consisting of EDTA and EGTA.

17. The method according to claim 14 further defined as adding a quantity of chelating agent sufficient to chelate available calcium ions.

18. The method according to claim 16 further defined as adding at least 1 micromole of the selected chelating agent per $10^9$ platelets in the platelet poor plasma.

19. The method according to claim 14 further defined as including the step of purifying FVIII/vWf from the plasma so treated.

20. A method of obtaining intact, non-degraded FVIII/vWf from blood or plasma containing FVIII/vWF and cellular sources of a calcium activated protease capable of cleaving the FVIII/vWf, said method comprising the steps of:

obtaining platelet poor plasma while avoiding release of the calcium activated protease from the cellular sources;

passing the platelet poor plasma through a filter capable of retaining particles 0.1 micron in size and larger for removing substantially all cellular sources of the calcium activated protease from the platelet poor plasma; and purifying FVIII/vWf from the filtered plasma.

* * * * *